United States Patent [19]

Grinter et al.

[11] Patent Number: 5,175,288

[45] Date of Patent: * Dec. 29, 1992

[54] PROCESS FOR PREPARING PURINE DERIVATIVES AND INTERMEDIATES THEREOF

[75] Inventors: Trevor J. Grinter; Graham R. Geen; Martin J. Parratt, all of Epsom, England

[73] Assignee: Beecham Group p.l.c., Brentford, England

[*] Notice: The portion of the term of this patent subsequent to May 21, 2008 has been disclaimed.

[21] Appl. No.: 506,587

[22] Filed: Apr. 9, 1990

Related U.S. Application Data

[63] Continuation of Ser. No. 226,295, Jul. 29, 1988, abandoned.

[30] Foreign Application Priority Data

Aug. 1, 1987 [GB] United Kingdom ............... 8718283
Jun. 13, 1988 [GB] United Kingdom ............... 8813926

[51] Int. Cl.⁵ ............... C07D 473/26; C07D 473/18; C07D 473/40
[52] U.S. Cl. .................... 544/230; 544/244; 544/264; 544/265; 544/271; 544/276; 544/277
[58] Field of Search ............... 544/276, 277, 244, 230, 544/264, 265, 271

[56] References Cited

U.S. PATENT DOCUMENTS

| | | | |
|---|---|---|---|
| 4,347,185 | 8/1982 | Muchowski et al. | 548/516 |
| 4,347,187 | 8/1982 | Muchowski et al. | 548/453 |
| 4,798,833 | 1/1989 | Johansson et al. | 514/262 |
| 4,845,084 | 7/1989 | Hannah et al. | 514/81 |
| 5,017,701 | 5/1991 | Grinter et al. | 544/276 |

FOREIGN PATENT DOCUMENTS

| | | |
|---|---|---|
| 0141927 | 5/1985 | European Pat. Off. |
| 0182024 | 5/1986 | European Pat. Off. ............ 544/277 |

OTHER PUBLICATIONS

Padgett, et al., J. Org. Chem., vol. 44, No. 20, pp. 3492-3496 (1979).
Csendes, et al., J. Org. Chem., vol. 44, No. 23, pp. 4173-4178 (1979).

Primary Examiner—Diana G. Rivers
Attorney, Agent, or Firm—Hopgood, Calimafde, Kalil, Blaustein & Judlowe

[57] ABSTRACT

A process for preparing pharmaceutically active compounds of formula (A):

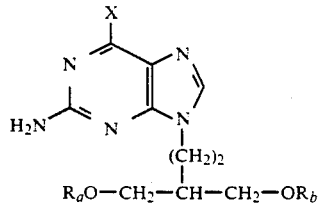

wherein X is hydrogen, hydroxy, chloro, $C_{1-6}$ alkoxy or phenyl $C_{1-6}$ alkoxy; and $R_a$ and $R_b$ are hydrogen, or acyl or phosphate derivatives thereof, which process comprises the preparation of an intermediate of formula (I):

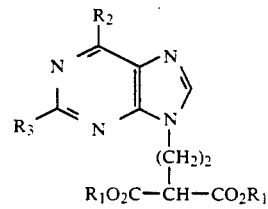

wherein $R_1$ is $C_{1-6}$ alkyl, or phenyl $C_{1-6}$ alkyl in which the phenyl group is optionally substituted; $R_2$ is hydrogen, hydroxy, chlorine, $C_{1-6}$ alkoxy, phenyl $C_{1-6}$ alkoxy or amino; and $R_3$ is halogen, $C_{1-6}$ alkylthio, $C_{1-6}$ alkylsulphonyl, azido, an amino group or a protected amino group, via the reaction of a compound of formula (II):

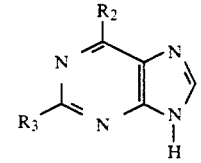

wherein $R_2$ and $R_3$ are as defined for formula (I) with:
(a) a compound of formula (III):

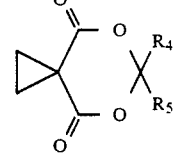

wherein $R_4$ and $R_5$ are independently hydrogen, $C_{1-6}$ alkyl, or phenyl, or $R_4$ and $R_5$ together are $C_{5-7}$ cycloalkyl; or
(b), a compound of formula (V):

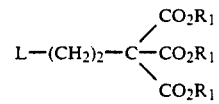

wherein L is a leaving group and $R_1$ is as defined for formula (I), and thereafter converting the resulting intermediates to a compound of formula (I) and converting a compound of formula (I) to a compound of formula (A).

8 Claims, No Drawings

PROCESS FOR PREPARING PURINE DERIVATIVES AND INTERMEDIATES THEREOF

This application is a continuation of application Ser. No. 226,295, filed Jul. 29, 1989.

The present invention relates to a chemical process for the preparation of novel compounds which are useful intermediates in the preparation of pharmaceutically active compounds, and to novel intermediates used in that process.

EP-A-0 141 927 and EP-A-0 182 024 describe, inter alia, compounds of formula (A):

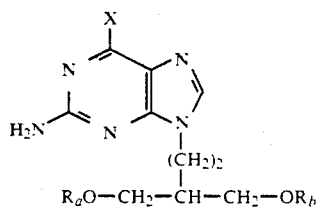

wherein X is hydrogen, hydroxy, chloro, $C_{1-6}$ alkoxy or phenyl $C_{1-6}$ alkoxy and $R_a$ and $R_b$ are hydrogen, including acyl and phosphate derivatives thereof.

The above publications disclose a process for the preparation of compounds of formula (A) which involves the reaction of purine derivatives, including compounds of formula (B):

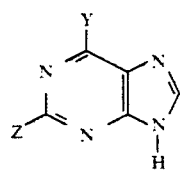

wherein Y is chloro, hydroxy, $C_{1-6}$ alkoxy, phenyl $C_{1-6}$ alkoxy or amino, and Z is chloro, amino or acylamino, with compounds of formula (C):

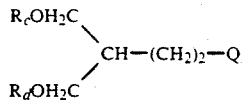

in which $R_c$ and $R_d$ are each independently acyl or together form a cyclic acetal or cyclic carbonate group and Q is a leaving group such as, chlorine, bromine or iodine, preferably iodine.

This process has the disadvantage that compounds of formula (C) are not readily available and must be prepared individually via multi-stage syntheses.

A new process for the preparation of compounds of formula (A) has now been discovered which uses a readily available or easily prepared starting material in place of the intermediates of formula (C).

According to the present invention there is provided a process for the preparation of a compound (A):

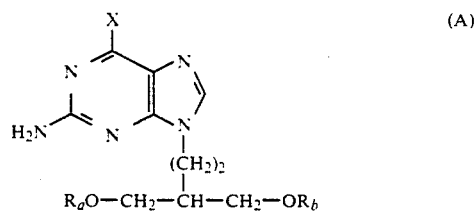

wherein:

X is hydrogen, hydroxy, chloro, $C_{1-6}$ alkoxy or phenyl $C_{1-6}$ alkoxy; and $R_a$ and $R_b$ are hydrogen, or acyl or phosphate derivatives thereof, which process comprises:

(i) the preparation of a compound of formula (I):

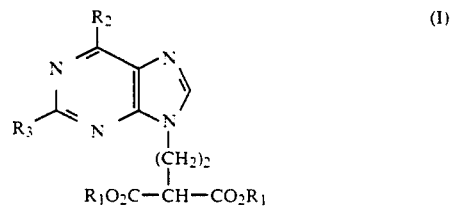

wherein $R_1$ is $C_{1-6}$ alkyl, or phenyl $C_{1-6}$ alkyl in which the phenyl group is optionally substituted; $R_2$ is hydrogen, hydroxy, chlorine, $C_{1-6}$ alkoxy, phenyl $C_{1-6}$ alkoxy or amino; and $R_3$ is halogen, $C_{1-6}$ alkylthio, $C_{1-6}$ alkylsulphonyl, azido, an amino group or a protected amino group, which preparation comprises the reaction of a compound of formula (II):

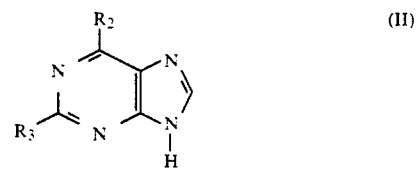

wherein $R_2$ and $R_3$ are as defined for formula (I)

With:

(a), a compound of formula (III):

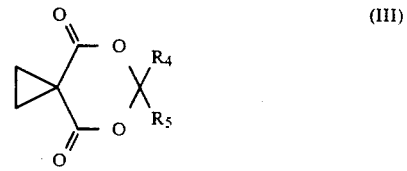

wherein $R_4$ and $R_5$ are independently hydrogen, $C_{1-6}$ alkyl, or phenyl, or $R_4$ and $R_5$ together are $C_{5-7}$ cycloalkyl, to give a compound of formula (IV):

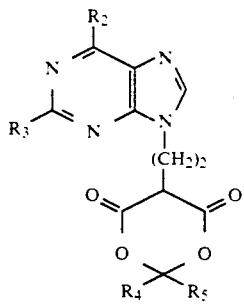

(IV)

or (b), a compound of formula (V):

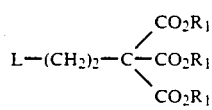

(V)

wherein L is a leaving group and $R_1$ is as defined for formula (I), to give a compound of formula (VI):

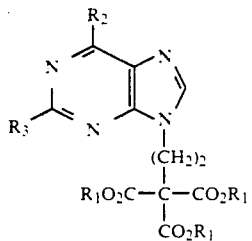

(VI)

and thereafter converting the intermediate compound of formula (IV) to a compound of formula (I) via transesterification, or the intermediate compound of formula (VI) to a compound of formula (I) via decarboxylation, and, as necessary or desired, interconverting variables $R_1$, $R_2$ and $R_3$ to further values of $R_1$, $R_2$ and $R_3$;

(ii) the conversion of the resulting compound of formula (I) to a compound of formula (A) by converting variable $R_3$, when other than amino, to amino, reducing the ester groups $CO_2R_1$ to $CH_2OH$ and optionally forming acyl or phosphate derivatives thereof, and as necessary or desired converting variable $R_2$ in the compound of formula (I) to variable X in the compound of formula (A).

As used herein, the term $C_{1-6}$ alkyl includes groups in which the alkyl moiety is straight or branched, favourably contains 1 to 4 carbon atoms and is preferably methyl. Substituents for phenyl when optionally substituted include one or two of hydroxy, $C_{1-6}$ alkyl, $C_{1-6}$ alkoxy and halogen, such as fluoro, chloro, bromo and iodo.

Values for X in compounds of formula (A) include hydrogen, hydroxy and $C_{1-6}$ alkoxy, for example methoxy. When X is hydroxy it will be appreciated that compounds of formula (A) exist in more than one tautomeric form.

Values for $R_a$ and $R_b$ in compounds of formula (A) include hydrogen and acyl such as $C_{2-5}$ alkanoyl, for example acetyl.

Values for $R_1$ in compounds of formula (I) include $C_{1-4}$ alkyl, for example methyl and ethyl.

Values for $R_2$ in compounds of formula (I) include hydrogen, chlorine, and $C_{1-4}$ alkoxy, for example methoxy.

Suitable values for $R_3$ when a protected amino group include $C_{2-5}$ alkanoylamino such as acetylamino or pivaloylamino, aroyl such as benzoyl, and arylmethyl such as benzyl.

Values for $R_3$ in compounds of formula (I) include amino, halogen for example chlorine, and protected amino such as $C_{2-5}$ alkanoylamino, for example acetylamino.

When $R_2$ in compounds of formula (II) is hydrogen, examples of $R_3$ include halogen for example chlorine, and amino. When $R_2$ in compounds of formula (II) is chlorine, examples of $R_3$ include halogen for example chlorine, amino, and acetylamino. Preferably $R_2$ in compounds of formula (II) is chlorine and $R_3$ in compounds of formula (II) is amino.

In process variant (a), values for $R_4$ and $R_5$ in compounds of formula (III) include hydrogen, $C_{1-4}$ alkyl for example methyl, phenyl and cyclohexyl. Preferably both $R_4$ and $R_5$ are methyl or one of $R_4$ and $R_5$ is hydrogen and the other is phenyl, $C_{1-4}$ alkyl such as methyl, or $R_4$ and $R_5$ together are cyclohexyl.

In process variant (b), the leaving group L in compounds of formula (V) is suitably a halogen atom, preferably bromine. Variable $R_1$ is preferably chosen such that a group $CO_2R_1$ is readily displaced from the intermediate compound of formula (VI) by decarboxylation. Preferably $R_1$ is an ethyl group.

The reaction of a compound of formula (II) with a compound of formula (III) according to process variant (a) or a compound of formula (V) according to process variant (b) may be carried out in an inert solvent for example dimethylformamide, dimethylsulphoxide or acetonitrile, preferably dimethylformamide, in the presence of an inorganic or organic base, over a temperature range from 0° C. to the boiling point of the solvent. Examples of inorganic bases include alkali metal hydrides, alkali metal carbonates such as sodium or potassium carbonate and preferably potassium carbonate. Suitable organic bases are 1,8-diazabicyclo[5.4.0]undec-7-ene and tetramethyl guanidine. The reaction conditions selected for the preparation of intermediate compounds of formulae (IV) and (VI) according to process variant (a) and (b) respectively may result in the isolation of these intermediate compounds as salts. For example, use of an alkali metal carbonate in process variant (a) may result in the isolation of the intermediate compound of formulae (IV) as the corresponding alkali metal salt.

Compounds of formula (I) may be obtained by transesterification of the compound of formula (IV) under conventional conditions, for example via acid catalysed reaction with the appropriate alcohol of formula (VII):

$R_1$-OH (VII)

wherein $R_1$ is as defined in formula (I). Advantageously $C_{1-6}$ aliphatic alcohols, for example methyl alcohol or ethyl alcohol, are used. An inert solvent may be added, if required.

The reaction may be carried out at temperatures ranging from ambient to the boiling point of the alcohol or inert solvent, if present.

Alternatively, compounds of formula (I) wherein $R_2$ is $OR_1$ may be obtained directly from compounds of formula (IV) wherein $R_2$ is chlorine via treatment with an alcohol of formula (VII), transesterification and displacement of chlorine by the group $OR_1$ taking place in the same reaction.

Compounds of formula (I) may be obtained by monodecarboxylation of the intermediate compounds of formula (VI). Decarboxylation may be carried out under conventional conditions, for example, by stirring at ambient temperature in the presence of a base such as sodium ethoxide in a solvent such as ethanol or tetrahydrofuran.

Compounds of formula (I) in which $R_2$ is chlorine, made by process variant (b), may be treated with an alcohol of formula (VII), as described above, to give a compound of formula (I) in which $R_2$ is $OR_1$. It will be appreciated that $R_1$ in compounds of formula (I) made by process variant (b) may be transesterified to further values of $R_1$ via reaction with an alcohol of formula (VII).

Intermediate compounds of formula (IV) and formula (VI) in which $R_2$ is chlorine may be hydrogenolysed to give intermediate compounds of formula (IV) and formula (VI) respectively in which $R_2$ is hydrogen, preferably by catalytic reduction using a noble metal catalyst, for example palladium on charcoal, in the presence of hydrogen or a hydrogen source such as ammonium formate, in an alcoholic solvent, preferably methanol or ethanol.

Variable $R_3$ in compounds of formula (I) may be converted to further values of $R_3$ using procedures conventionally practised in purine chemistry. For example, an amine protecting group such as arylmethyl may be removed by hydrogenolysis. Where the intermediate compounds of formulae (IV) and (VI) are subjected to hydrogenolysis reactions as described above, the protecting group will be removed at this intermediary stage. Similarly, variable $R_3$ may be converted from azido to amino by catalytic reduction, and an $R_3$ halogen, alkylthio or alkylsulphonyl group may be converted to an $R_3$ amino group by aminolysis using, for example, ammonia.

Variables $R_1$ and $R_2$ may of course be susceptible to the reaction conditions chosen for interconversion of variable $R_3$. It will be apparent to the skilled chemist that the process variant [(a) or (b)] followed, and the stage in the reaction sequence at which the transformation of variables, where necessary or desired, is carried out, may be chosen to suit the variables $R_1$, $R_2$ and $R_3$ required in the compound of formula (I).

The compounds of formulae (I), (IV) and (VI) are novel compounds and form part of the present invention. Compounds of formulae (I), (IV) and (VI) may form salts and solvates such as hydrates, and the invention also extends to these forms. Some of the compounds of formula (III) are known compounds. The compound of formula (III) in which $R_3$ and $R_4$ are methyl may be prepared according to the procedure described in Organic Syntheses, (Vol. 60, P. 66). Other compounds of formula (III) may be prepared by analogous procedures. The alcohols of formula (VII) are known compounds or are prepared by analogous procedures to those used to prepare known compounds of formula (VII).

Certain compounds of formula (V) are known compounds. The compound of formula (V) in which L is bromine and $R_1$ is ethyl may be prepared from commercially available triethyl methanetricarboxylate according to the procedure described by H. Rapoport et al, [Journal of Organic Chemistry, 44. 3492 (1979)]. Other compounds of formula (V) may be prepared by an analogous procedure. Methane tricarboxylate derivatives may be prepared by standard methods from the corresponding malonic acid derivatives.

Purine derivatives of formula (II) are generally known compounds and their preparation is described in the prior art relating to purine chemistry. The compound of formula (II) in which $R_2$ is chlorine and $R_3$ is an amino group is 2-amino-6-chloropurine, utilised in the process of the Examples disclosed in EP-A-0 141 927.

The compounds of formula (I) in which $R_2$ is hydrogen, hydroxy, chloro, $C_{1-6}$ alkoxy or phenyl $C_{1-6}$ alkoxy and $R_3$ is an amino group may be reduced under conventional conditions, for example using sodium borohydride, to the compounds of formula (A) in which X is hydrogen, hydroxy, chloro, $C_{1-6}$ alkoxy or phenyl $C_{1-6}$ alkoxy and $R_a$ and $R_b$ are hydrogen. The compound of formula (A) in which X is hydroxy and $R_a$ and $R_b$ are hydrogen may be obtained under conventional hydrolysis conditions, for example in aqueous sodium hydroxide solution, from compounds of formula (A) in which X is $C_{1-6}$ alkoxy or phenyl $C_{1-6}$ alkoxy and $R_1$ and $R_b$ are hydrogen. Compounds of formula (A) in which X is hydrogen or hydroxy and $R_a$ and $R_b$ are hydrogen may be converted to further compounds of formula (A) in accordance with the procedures described in EP-A-0 182 024 and EP-A-0 141 927.

The following Descriptions and Examples illustrate the process and novel compounds of the invention. The use of the novel compounds of the invention in the preparation of compounds of formula (A) is included by way of illustration.

DESCRIPTION 1

2-Amino-6-chloro-9-1-(2,2-dimethyl-1,3-dioxane-4,6-dione-5-yl)eth-2-yl]purine potassium salt

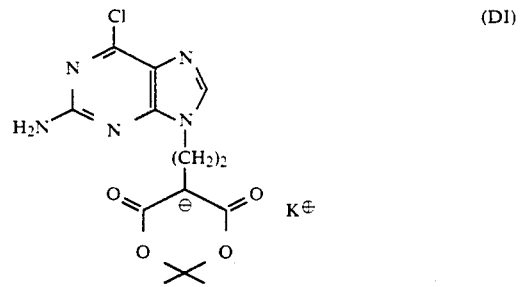

(DI)

A mixture of 2-amino-6-chloropurine (0.5 g, 2.94 mmol), 6,6-dimethyl-5,7-dioxaspiro[2.5]octane-4,8-dione (0.5 g, 2.94 mmol) and potassium carbonate (0.49 g, 3.53 mmol) in N,N-dimethylformamide (10 ml) was stirred at room temperature under dry nitrogen overnight. T.l.c. [chloroform/methanol (2:1)] showed two products, rf=0.21, 0.34. The mixture was filtered and the filtrate evaporated to leave an oil which was triturated with dichloromethane (5 ml) to give a cream coloured solid. The solid was dissolved in chloroform/methanol (3:1) (7.8 ml) and column chromatographed on silica (125 g) (eluant=chloroform/methanol (3:1) gradually increasing to (1:1)) to give the title compound (0.51 g, 46%), rf [chloroform/methanol (2:1)]=0.34 and 2-amino-6-chloro-7-[1-(2,2-dimethyl-1,3-dioxane-4,6- dione-5-yl)eth-2-yl]purine potassium salt (0.23 g, 21%), rf [chloroform/methanol (2:1)]=0.21

¹H n.m.r. (CD₃OD) of title compound: δ1.50(s,6H,—CH₃), 2.72(t,2H,³J$_{HH}$=8 Hz,—CH₂—), 4.20(t,2H,³J$_{HH}$=8 Hz, >NCH₂—), 8.05(s,1H,H-8).

Decomposition occurs at 290° C.

DESCRIPTION 2

2-Amino-9-[1-(2,2-dimethyl-1,3-dioxane-4,6-dione-5-yl)-eth-2-yl]purine potassium salt

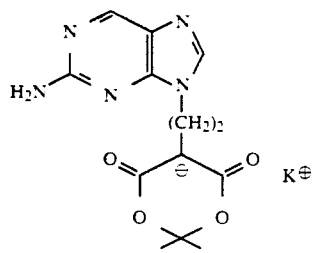

(D2)

A mixture of 2-amino-6-Chloro-9-[1-(2,2-dimethyl-1,3-dioxane-4,6-dione-5-yl)eth-2-yl]purine potassium salt (200 mg, 0.53 mmol), ammonium formate (148 mg, 2.34 mmol) and 10% palladuim on charcoal (80 mg) in methanol (15 ml) was heated under reflux under dry nitrogen for 3 h. T.l.c. [chloroform/methanol (2:1)] showed one spot, rf=0.15. The mixture was filtered and the filtrate evaporated to leave a gum. The material was not purified further.

¹H n.m.r. (D₂O): δ1.45(s,6H.—CH₃), 2.65(t,2H,³J$_{HH}$=8 Hz, —CH₂—), 4.20(t,2H,³J$_{HH}$=8 Hz, >NCH₂—), 8.05(s,1H,H-8), 8.50(s,1H,H-6).

DESCRIPTION 3

6-Phenyl-5,7-dioxaspiro[2.5]octane-4,6-dione

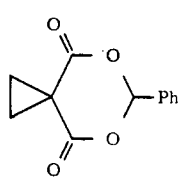

(D3)

To a suspension of cyclopropane-1,1-dicarboxylic acid (1.0 g, 7.69 mmol) in a mixture of acetic anhydride (0.86 g, 8.45 mmol) and benzaldehyde (0.81 g, 7.63 mmol) stirred at room temperature was added one drop of concentrated sulphuric acid. The suspension immediately became a light brown solution which, after two minutes turned into a pink solid. The reaction mixture was partitioned between water (100 ml) and dichloromethane (2×100 ml). The combined organic extracts were dried (MgSO₄), filtered and evaporated to leave a white solid which was triturated with ether/hexane (1:1) (15 ml) to leave 0.70 g (42%) of white solid material, rf[ether/hexane (3:2)]=0.40, mp 131°-131.5° C.

¹H n.m.r (CDCl₃): δ1.90(s,4H,—CH₂—), 6.80(s,1H,—O—CHPhO—), 7.45(brs,5H,—C₆H₅).

DESCRIPTION 4

2-Amino-6-chloro-9-[1-(2-phenyl-1,3-dioxane-4,6-dione-5-yl)eth-2-yl]purine potassium salt

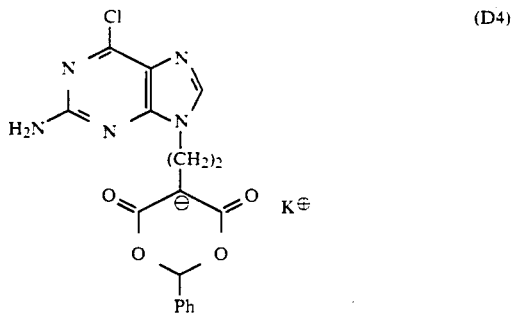

(D4)

A mixture of 2-amino-6-chloropurine (0.23 g, 1.36 mmol), 6-phenyl-5,7-dioxaspiro[2.5]octane-4,8-dione (0.30 g, 1.37 mmol) and potassium carbonate (0.22 g, 1.59 mmol) in N,N-dimethylformamide (5 ml) was stirred at room temperature under dry nitrogen overnight T.l.c. [chloroform/methanol (2:1)] showed two products, rf=0.45, 0.55. The mixture was filtered and the filtrate evaporated to leave an oil which was triturated with dichloromethane (15 ml) to give a cream coloured solid. The solid was purified by column chromatography on silica (65 g) [eluent=dichloromethane/methanol (4:1) gradually increasing to (1:1)] to give the title compound (0.21 g, 36%), rf[chloroform/methanol (2:1)]=0.55 and 2-amino-6-chloro-7-[1-(2-phenyl-1,3-dioxane-4,6-dione-5-yl)eth-2-yl]purine potassium salt (0.14 g, 24%), rf[chloroform/methanol (2:1)]=0.45.

¹H n.m.r (D⁶-DMSO): of the title compound: δ2.55 (m,2H,—CH₂—), 4.20(m,2H, >NCH₂—), 6.80(brs,2H,—NH₂), 7.50(brs, 6H, —C₆H₅+—OCHPhO—), 8.10(s,1H,H-8).

DESCRIPTION 5

5,12-Dioxadispiro[2.2.5.2]tridecane-4,13-dione

(D5)

A mixture of cyclopropane-1,1-dicarboxylic acid (13.0 g, 0.10 mmol), cyclohexanone (10.8 g, 0.11 mol), acetic anhydride (11.2 g, 0.11 mol) and concentrated sulphuric acid (5 drops) was stirred at room temperature 0.5 h. The mixture soon became a wine-red solution which later darkened to purple. The reaction mixture was partitioned between water (100 ml) and ether (2×100 ml). The combined organic extracts were washed with brine (50 ml), dried (MgSO₄), filtered and evaporated to leave a purple oil plus some solid material. This mixture was purified by column chromatography on silica [eluent=ether/hexane (4:1)] to give the title compound as colourless crystals (2.70 g, 13%), m.p. 134.5°-135° C.

¹H n.m.r (CDCl₃) δ1.35-2.18(m,10H,cyclohexyl—CH₂—), 1.93(s,4H,cyclopropyl—CH₂—).

DESCRIPTION 6

2-Amino-6-chloro-9-[1-[1,5-dioxaspiro[5.5]undecane-2,4-dione-3-yl]eth-2-yl]purine potassium salt

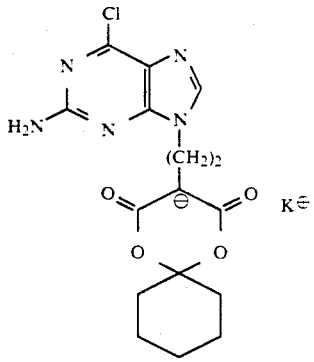
(D6)

A mixture of 2-amino-6-chloropurine (0.80 g, 4.72 mmol), 5,12-dioxaspiro[2.2.5.2]tridecane-4,13-dione (1.0 g, 4.80 mmol) and potassium carbonate (1.0 g, 7.23 mmol) in N,N-dimethylformamide (10 ml) was stirred at room temperature under dry nitrogen for 36 h. The mixture was filtered and the filtrate evaporated to give a thick foam (2.7 g) which was shown by $^1$H n.m.r. analysis to be a mixture of the title compound and 2-amino-6-chloro-7-[1-[1,5-dioxaspiro[5.5]undecane-2,4-dione-3-yl]eth-2-yl]purine potassium salt in the ratio of 2:1 respectively.

$^1$H n.m.r (D$^6$-DMSO) of the title compound: δ1.25–2.25(m,10H,cyclohexyl—CH$_2$—), 3.02(m, 2H.—CH$_2$—), 3.78(t,2H,$^3$J$_{HH}$=8 Hz, >NCH$_2$—),6.77(brs,2H,—NH$_2$), 8.13 (s,1H,H-8).

DESCRIPTION 7

2-Acetylamino-6-chloro-9-[1-(2,2-dimethyl-1,3-dioxane-4,6-dione-5-yl)eth-2-yl]purine potassium salt

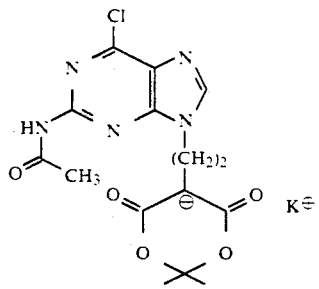
(D7)

A mixture of 2-acetylamino-6-chloropurine1 (1.0g, 4.72 mmol), 6,6-dimethyl-5,7-dioxaspiro[2.5]octane-4,8-dione (0.80 g, 4.70 mmol) and potassium carbonate (0.78 g, 5.64 mmol) in N,N-dimethylformamide (25 ml) was stirred at room temperature under dry nitrogen overnight. T.l.c.[chloroform/methanol(2:1)] showed two products, rf=0.50, 0.65. The mixture was filtered and the filtrate evaporated to leave a light brown gum which was triturated with dichloromethane (30 ml) to leave a pale yellow solid (2.0 g) which was shown by $^1$H n.m.r. analysis to be a mixture of the title compound and 2-acetylamino-6-chloro-7-[1-(2,2-dimethyl-1,3-dioxane-4,6-dione-5-yl)eth-2-yl]purine potassium salt in the ratio of 3:2 respectively.

1. W. A. Bowles, F. H. Schneider, L. R. Lewis and R. K. Robins, J. Med. Chem., 6, 471, (1963).

$^1$H n.m.r (D$^6$-DMSO) of the title compound: δ1.40(s,6H,—CH$_3$), 2.25(s,3H.—COCH$_3$), 2.65(t,2H,$^3$J$_{HH}$=8 Hz, —CH$_2$—), 4.20(t,2H,$^3$J$_{HH}$=8 Hz, >NCH$_2$—), 8.35(s,1H,H-8).

DESCRIPTION 8

2-Amino-9-[1-(2,2-dimethyl-1,3-dioxane-4,6-dione-5-yl)eth-2-yl]purine potassium salt

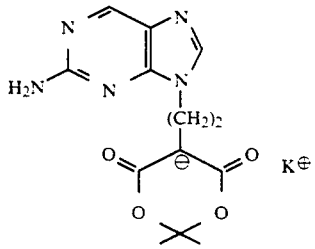
(D8)

A mixture of 2-aminopurine2 (200 g, 1.48 mmol), 6,6-dimethyl-5,7-dioxaspiro[2.5]octane-4,8-dione (252 mg, 1.48 mmol) and potassium carbonate (245 mg, 1.77 mmol) in N,N-dimethylformamide (5 ml) was stirred at room temperature under dry nitrogen overnight. T.l.c. [chloroform/methanol (2:1)] showed two products, rf=0.23, 0.33. The mixture was evaporated and the residue purified by column chromatography on silica (25 g) [eluent=chloroform/methanol (2:1)] to give the the title compound (250 mg, 49%), rf[chloroform/methanol (2:1)]=0.33 and 2-amino-7-[1-(2,2-dimethyl-1,3-dioxane-4,6-dione-5-yl)eth-2-yl]purine potassium salt (150 mg, 29%), rf[chloroform/methanol (2:1)]=0.23.

2. A. Albert and D. J. Brown, J. Chem. Soc., 2060, (1954).

$^1$H n.m.r (D$^6$-DMSO) of the title compound: δ1.35(s,6H,—CH$_3$), 2.52(t,2H,$^3$J$_{HH}$=8 Hz,—CH2—), 4.20(t,2H,$^3$J$_{HH}$=8 Hz,>NCH$_2$—), 8.05(s,1H,H-8), 8.60 (s,1H, H-6).

DESCRIPTION 9

2-Chloro-9-[1-(2,2-dimethyl-1,3-dioxane-4,6-dione-5-yl)eth-2-yl]purine potassium salt

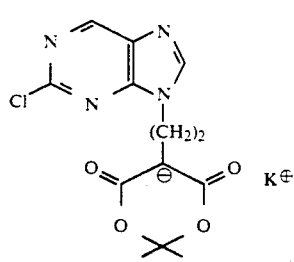
(D9)

A mixture of 2-chloropurine3 (229 mg, 1.48 mmol), 6,6-dimethyl-5,7-dioxaspiro[2.5]octane-4,8-dione (252 mg, 1.48 mmol) and potassium carbonate (245 mg, 1.77 mmol) in N,N-dimethylformamide (5 ml) was stirred at room temperature under dry nitrogen for 66 h. T.l.c. [chloroform/methanol (2:1)] showed one spot, rf=0.45. The mixture was evaporated and the residue purified by column chromatography on silica (35 g) [eluent=dichloromethane/methanol (9:1) gradually increasing to (1:1)] to give a white solid (340 mg) which was shown by $^1$H n.m.r analysis to be a mixture of the title compound and 2-chloro-7-[1-(2,2-dimethyl-1,3-dioxane-4,6- dione-5-yl)eth-2-yl]purine potassium salt in the ratio of 3:2 respectively.

3J. A. Montgomery, J. Am. Chem. Soc., 78, 1928, (1956).

¹H n.m.r. (D⁶-DMSO) of the title compound: δ61.55 (s,6H,—CH₃), 2.60 (m, 2H, —CH₂—), 4.45 (m, 2H, >NCH₂—), 8.60 (s, 1H, H-8), 9.10 (s, 1H, H-6).

DESCRIPTION 10

2,6-Dichloro-9-[1-(2,2-dimethyl-1,3-dioxane-4,6-dione-5-yl)eth-2-yl]purine potassium salt

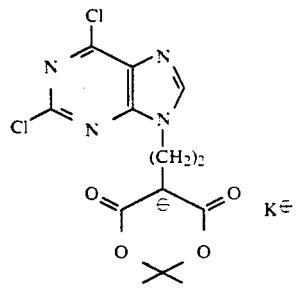

(D10)

A mixture of 2,6-dichloropurine4 (95 mg, 0.50 mmol), 6,6-dimethyl-5,7-dioxapiro[2.5]octane-4,8-dione (85 mg, 0.50 mmol) and potassium carbonate (83 mg, 0.60 mmol) in N,N-dimethylformamide (2 ml) was stirred at room temperature under dry nitrogen overnight. T.l.c. [chloroform/methanol(2:1)] showed one spot, rf=0.55. The mixture was evaporated and the residue partitioned between water (10 ml) and dichloromethane (5 ml). The aqueous layer was evaporated to leave a light brown gum which was purified by column chromatography on silica (25 g)[eluent=chloroform/methanol (4:1) gradually increasing to (2:1)] to give a colourless glassy material (150 mg) which was shown by ¹H n.m.r. analysis to be a mixture of the title compound and 2,6-dichloro-7-[1-(2,2-dimethyl-1,3-dioxane-4,6-dione-5-yl)eth-2-yl]purine potassium salt in the ratio of 3:2 respectively.

4. U.S. Pat. No. 3,314,938, 1967.

¹H n.m.r. (D₂O) of title compound: δ1.45(s,6H,—CH₃), 2.60(m, 2H, >NCH₂—), 8.45 (s, 1H, H-8).

DESCRIPTION 11

2-Amino-6-chloro-9-(ethyl 2,2-dicarboethoxybutanoate-4-yl)purine

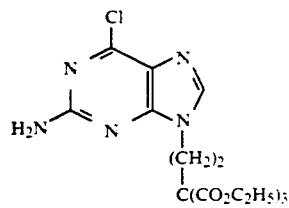

(D11)

Ethyl 4-bromo-2,2-dicarboethoxybutanoate (93 g) was added to a stirred mixture of 2-amino-6-chloropurine (47 g) and anhydrous potassium carbonate (57 g) in N,N-dimethylformamide (1 dm³) and the resulting mixture stirred at 40° C. overnight. The reaction mixture was filtered and the filtrate evaporated. Ethyl acetate (1000 cm³) was added to the residue and the solution washed with water (3×500 cm³) and brine (500 cm³). After drying over magnesium sulphate the solution was evaporated to give a yellow solid. T.l.c. (5% methanol-dichloromethane) showed two products, rf=0.42, 0.58; corresponding to the N7- and N9- alkylated purines.

Recrystallisation from butan-1-ol (350 cm³) gave 43 g (37%) of the title compound. Column chromatography on silica (eluant 5% methanol-chloroform) of the filtrate gave a further 22 g (19%) of the desired material, m.p. 107°–108° C.

¹H n.m.r. (D⁶-DMSO): δ1.20(t,9H,—CH₂CH₃), 2.65(t,2H,

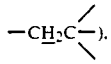

4.20(q,6H, —CH₂CH₃), 4.35(t,2H, >N—CH₂), 6.95 (brs, 2H, —NH₂), 8.10 (s,1H, H-8).

DESCRIPTION 12

2-Amino-9-(ethyl 2,2-dicarboethoxybutanoate-4-yl)purine

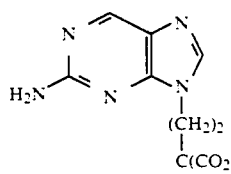

(D12)

A mixture of 2-amino-6-chloro-9-(ethyl 2,2-dicarboethoxybutanoate-4-yl)purine (21.4 g), prepared as in Description 11, ammonium formate (20 g) and 5% palladium on charcoal (4 g) in methanol (200cm³) was heated under reflux under nitrogen for 2 hours. After cooling, the mixture was filtered and the filtrate evaporated to a gum. The gum was dissolved in water (400 cm³), extracted with chloroform (3×200 cm³) and the combined extract dried over magnesium sulphate. Filtration and evaporation gave the title compound as an oil 18.7 g (95%) which slowly crystallised on standing. m.p. 58°-60° C.

¹H n.m.r. (D⁶-DMSO): 61.20(t,9H, —CH₂CH₃), 2.65 (t, 2H,

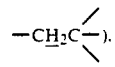

4.15(q,6H, —CH₂CH₃), 4.35(t,2H, >N—CH₂), 6.50(brs, 2H, —NH₂), 7.95(s,1H,H-8), 8.65(s,1H,H-6).

EXAMPLE 1

2-Amino-9-(methyl 2-carbomethoxybutanoate-4-yl)purine

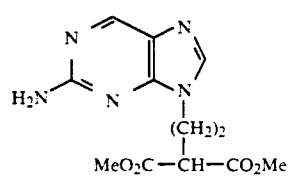

(E1)

The crude 2-amino-9-[1-(2,2-dimethyl-1,3-dioxane-4,6-dione-5-yl)eth-2-yl)]purine potassium salt from Description 2 was suspended in methanol (10 ml) saturated with hydrogen chloride, the mixture diluted with methanol (10 ml) and stirred overnight at room temperature, giving a clear, colourless solution. T.l.c. [chloroform/methanol (9:1)] showed one spot, rf=0.45. The mixture was evaporated, the residue dissolved in water (20 ml) and the solution neutralized using saturated aqueous sodium bicarbonate solution. The aqueous solution was then extracted with dichloromethane (6×25 ml), the combined extracts dried over magnesium sulphate, filtered and evaporated to leave the title compound (142 mg, 82%) as an oil.

$^1$H n.m.r. (CDCl$_3$) δ2.40(q,2H,$^3J_{HH}$=8 Hz,—CH$_2$—), 3.35 (t,1H,$^3J_{HH}$=8 Hz,>CH—), 3.65(s,6H,—CH$_3$), 4.15(t,2H, $^3J_{HH}$=8 Hz,>NCH$_2$—), 5.35(brs,2H,—NH$_2$), 7.70(s, 1H,H-8), 8.62(s,1H,H-6).

EXAMPLE 2

2-Amino-6-methoxy-9-(methyl 2-carbomethoxybutanoate-4-yl)purine

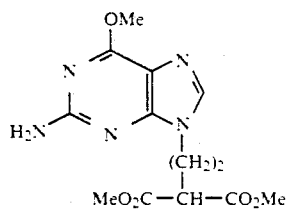

(E2)

2-amino-6-chloro-9-[1-(2,2-dimethyl-1,3-dioxane-4,6-dione-5-yl)eth-2-yl]purine, potassium salt (1.70 g, 4.50 mmol), prepared as in Description 1, was suspended in methanol (35 ml) saturated with hydrogen chloride, the mixture diluted with methanol (35 ml) and stirred at room temperature overnight giving a clear, pale yellow solution. T.l.c. [chloroform/methanol (9:1)] showed one spot, rf=0.65 The mixture was evaporated under reduced pressure, the residue dissolved in water (70 ml) and the solution neutralized using saturated aqueous sodium bicarbonate solution. The aqueous solution was then extracted with dichloromethane (5×100 ml), the combined extracts dried over magnesium sulphate, filtered and evaporated to leave the title compound (1.27 g, 87%) as a colourless viscous oil, a sample of which was recrystallised from water to give colourless needles.

m.p 108°-109° C.

$^1$H n.m.r. (CDCl$_3$): δ2.47(q,2H,$^3J_{HH}$=7 Hz,—CH—); 3.40 (t,1H,$^3J_{HH}$=7 Hz,>CH—); 3.75(s, 6H,—CO$_2$CH$_3$); 4.10 (s,3H, —OCH$_3$); 4.20(t,2H,$^3J_{HH}$=7 Hz,>NCH$_2$—); 4.95(brs,2H,—NH$_2$); 7.60 (s,1H,H-8).

EXAMPLE 3

2-Amino-9-(ethyl 2-carboethoxybutanoate-4-yl)purine

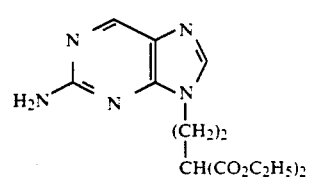

(E3)

2-Amino-9-(ethyl 2,2-dicarboethoxybutanoate-4-yl)purine (3.93 g) in ethanol (25cm$^3$), prepared as in Description 12, was added to a solution of sodium (0.7 g) in ethanol (15 cm$^3$) and the mixture stirred at ambient temperature for 1 hour. T.l.c. (10% methanol-chloroform) showed one spot, rf=0.36. The reaction mixture was acidified to pH 3 with dilute hydrochloric acid (ca. 15 cm$^3$) and the solvent evaporated. The residue was extracted with dichloromethane (2×250 cm$^3$) and the combined extract dried over magnesium sulphate. Filtration and evaporation gave a yellow oil.

The oil was dissolved in dichloromethane (ca. 10 cm$^3$) and column chromatographed on silica (100 g) (eluant 5% methanol-dichloromethane) to give the title compound 1.9 g (59%) as an oil which crystallised on standing at ambient temperature. m.p. 65°-66° C.

$^1$H n.m.r. (D$^6$-DMSO): δ1.15(t,6H, —CH$_3$CH$_3$), 2.35 (q, 2H, —CH$_2$CH<), 3.50 (t,1H, —CH<), 4.05 (dq, 4H, —CH$_2$CH$_3$), 4.20 (m,2H, >N—CH$_2$), 6.55(brs. 2H, —NH$_2$), 8.05 (s, 1H, H-8), 8.60 (s,1H, H-6).

PREPARATION OF COMPOUNDS OF FORMULA (A)

a)

2-Amino-9-(4-hydroxy-3-hydroxymethylbut-1-yl)purine

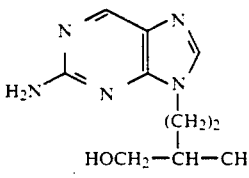

The compound of Example 1, 2-amino-9-(methyl-2-carbomethoxybutanoate-4-yl)purine (0.11 g, 0.38 mmol) was dissolved in t-butanol (4.5 ml) at 60° C. under dry nitrogen. Sodium borohydride (84 mg, 2.22 mmol) was added, the mixture heated to reflux and methanol (0.4 ml) added slowly over 2 h. The mixture was cooled, water (10 ml) was added and the solution was neutralized using dilute aqueous hydrochloric acid. The solution was evaporated to leave a white solid which was column chromatographed on silica (20 g) [eluant=chloroform/methanol (2:1)] to give the title compound (50 mg, 55%) as a white solid, rf [chloroform/methanol (2:1)]=0.40.

$^1$H n.m.r.(D$_2$O): δ1.85(m,3H,—CH$_2$—+>CH—), 3.65(d,4H,$^3J_{HH}$=5 Hz,—CH$_2$O—), 4.17(t,2H,$^3J_{HH}$=6 Hz, >NCH$_2$—), 8.12(s,1H,H-8), 8.53(s,1H,H-6).

b)

2-Amino-9-(4-hydroxy-3-hydroxymethylbut-1-yl)purine

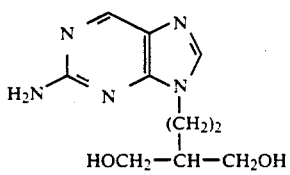

The compound of Example 3, 2-amino-9-(ethyl 2-carboethoxybutanoate-4-yl)purine (3.21 g) was dissolved in t-butanol (100 cm$^3$) at 60° C. Sodium borohydride (2.3 g) was added and the mixture heated to reflux. Methanol (10 cm$^3$) was added dropwise over 1 hour with vigorous stirring. The mixture was cooled, water (150 cm$^3$) added and the solution neutralised using dilute hydrochloric acid. After evaporation the residue was extracted with methanol (100 cm³) and the mixture filtered. The filtrate was evaporated to leave a yellow gum, t.l.c. (35% methanol-chloroform) showed this to be the desired material, rf 0.40. Purification via column chromatography on silica (100 g) [eluant =30% methanol-chloroform] gave the title compound 1.2 g (50.5%) as an off-white solid. m.p. 154° C.

¹H n.m.r. (D⁶-DMSO) δ1.45(m, 1H, —CH<), 1.80 (q, 2H, —CH₂CH<), 3.35 (m,2H,—OCH₂), 3.40 (m,2H,—OCH₂—), 4.10 (t,2H, >N—CH₂), 4.40 (t,2H,—OH), 6.50 (brs, 2H,—NH2), 8.10 (s,1H,H-8), 8.60 (s,1H,H-6).

c)
9-(4-Acetoxy-3-acetoxymethylbut-1-yl)-2-aminopurine

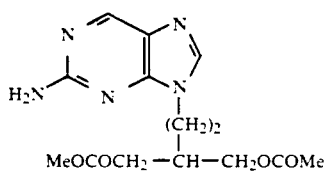

MeOCOCH₂—CH—CH₂OCOMe

To a suspension of 2-amino-9-(4-hydroxy-3-hydroxymethylbut-1-yl)purine (0.13 g, 0.55 mmol) in dry tetrahydrofuran (40 ml). stirred at room temperature under dry nitrogen were added pyridine (117 μl, 1.45 mmol) and 4-dimethylaminopyridine (5 mg, 41 μmol) followed by acetic anhydride (108 μl, 1.14 mmol). The mixture was stirred at room temperature for 5 h. giving a clear, colourless solution. T.l.c. [chloroform/methanol (9:1)] showed the major product to be the title compound. rf=0.40. Methanol (5 ml) was added, the mixture stirred for 5 mins. then evaporated to dryness. The residue was partitioned between water (5 ml) and chloroform (10 ml). The aqueous portion was extracted with chloroform (4×10 ml) then the combined organic portions dried over magnesium sulphate, filtered and evaporated to leave a pale yellow glassy material which was column chromatographed on silica (20 g) [eluant=-chloroform/methanol (19:1)] to give the title compound (0.16 g, 91%) as a colourless viscous oil, which was crystallised from n-butanol (0.6 ml) to give colourless crystals (118 mg., 67%). m.p. 102° C.

¹H n.m.r(CDCl₃) 61.90(m,3H,—CH₂—+>CH—), 2.00(s,6H.—CH₃), 4.05(d,4H,³J_HH=5 Hz,—CH₂—O), 4.10(t,2H,³J_HH=6 Hz,>NCH₂—), 5.35(br.s,2H,—NH₂), 7.70(s,1H,H-8), 8.60(s,1H,H-6).

d)
2-Amino-6-methoxy-9-(4-hydroxy-3-hydroxymethylbut-1-yl)purine

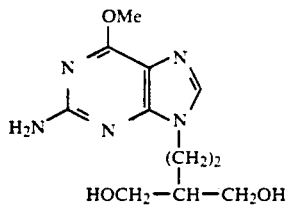

HOCH₂—CH—CH₂OH

2-Amino-6-methoxy-9-(methyl 2-carbomethoxybutanoate-4-yl)purine (130 mg, 0.40 mmol) was dissolved in t-butanol (5.8 ml) at 60° C. under dry nitrogen. Sodium borohydride (100 mg, 2.64 mmol) was added, the mixture heated to reflux and methanol (0.58 ml) added slowly over 2.5 h. The mixture was cooled, water (10 ml) added and the resulting solution neutralized using dilute aqueous hydrochloric acid. The solution was evaporated under reduced pressure to leave a white solid which was column chromatographed on silica (50 g) [eluant=chloroform/methanol (4:1)] to give the title compound (81 mg, 76%) as a colourless viscous oil, rf[chloroform/methanol (2:1)]=0.5, a sample of which was crystallised from n-butanol to give a cream-coloured solid, m.p. 84°-86° C.

¹H n.m.r.(D₂O): δ1.76(sept.,1H,³J_HH=7 Hz,>CH—), 1.87(q,2H,³J_HH=7 Hz,—CH₂—), 3.65(dd,2H,²J_HH=14 Hz, ³J_HH=7 Hz,—CHH'O—), 3.70(dd,2H,²J_HH=14 Hz,³J_HH=7 Hz, —CHH'O—), 4.05(s,3H,—OCH₃), 4.10(t,2H,³J_HH=7 Hz,>NCH₂), 7.80(s,1H,H-8).

e) 9-(4-Hydroxy-3-hydroxymethylbut-1-yl)quanine

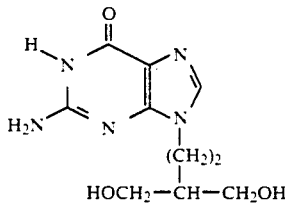

HOCH₂—CH—CH₂OH

2-Amino-6-methoxy-9-(4-hydroxy-3-hydroxymethylbut-1-yl)purine (360 mg, 1.35 mmol) was dissolved in 2M aqueous sodium hydroxide solution (20 ml) and the mixture heated at 80° C. for 2 h. The mixture was cooled, neutralized using 2M aqueous hydrochloric acid and evaporated down to a volume of approximately 20 ml under reduced pressure then left to stand at 4° C. for 18 h. The resulting precipitate was filtered off to give a white powder (260 mg, 76%), a sample of which was recrystallized from water to give colourless crystals. m.p. 275°-277° C.

¹H n.m.r.(D⁶-DMSO):δ1.50(m,1H,>CH—), 1.75(q,2H,³J_HH=7 Hz,—CH₂—), 3.43(m,4H,—CH₂O—), 4.40(t,2H,³J_HH=7 Hz,>NCH₂—),6.40(brs,2-H,—NH₂), 7.70(s,1H,H-8),10.50(brs,1H,H-1).

We claim:

1. A process for the preparation of a compound of formula (A):

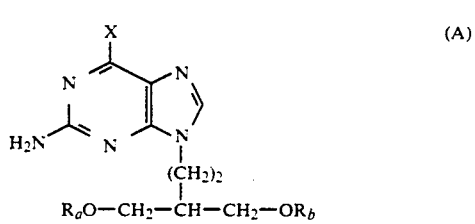

(A)

R_aO—CH₂—CH—CH₂—OR_b wherein:

X is hydrogen, hydroxy, chloro, C_{1-6} alkoxy or phenyl C_{1-6} alkoxy; and R_a and R_b are hydrogen, C_{2-5} alkanoyl or phosphate derivatives thereof, which process comprises:

(i) the preparation of a compound of formula (I):

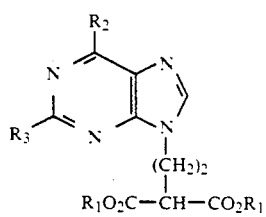

wherein $R_1$ is $C_{1-6}$ alkyl, or phenyl $C_{1-6}$ alkyl in which the phenyl group is optionally substituted with one or two substituents selected from the group consisting of hydroxy, $C_{1-6}$ alkyl, $C_{1-6}$ alkoxy or halogen; $R_2$ is hydrogen, hydroxy, chlorine, $C_{1-6}$ alkoxy, phenyl $C_{1-6}$ alkoxy or amino; and $R_3$ is halogen, $C_{1-6}$ alkylthio, $C_{1-6}$ alkylsulphonyl, azido, an amino group $C_{2-5}$ alkanoylamino, benzoylamino or benzylamino, which preparation comprises the reaction of a compound of formula (II):

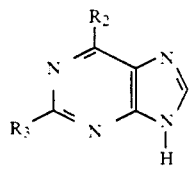

wherein $R_2$ and $R_3$ are as defined for formula (I) with: (a). a compound of formula (III):

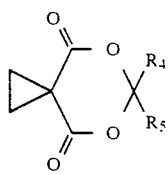

wherein $R_4$ and $R_5$ are independently hydrogen, $C_{1-6}$ alkyl, or phenyl, or $R_4$ and $R_5$ together are $C_{5-7}$ cycloalkyl, to give a compound of formula (IV):

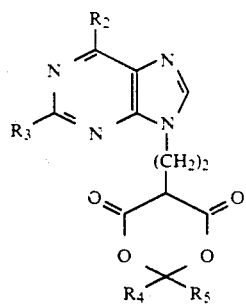

and thereafter converting the intermediate compound of formula (IV) to a compound of formula (I) via transesterification, and, as necessary or desired, interconverting variables $R_1$, $R_2$ and $R_3$ to further values of $R_1$, $R_2$ and $R_3$; and thereafter
(ii) the conversion of the resulting compound of formula (I) to a compound of formula (A) by
a. converting variable $R_3$, when other than amino, to amino, b. reducing the ester groups $CO_2R_1$ to $CH_2OH$ and optionally forming $C_{2-5}$ alkanoyl or phosphate derivatives thereof, and c. as necessary or desired converting variable $R_2$ in the compound of formula (I) to variable X in the compound of formula (A).

2. A process for the preparation of a compound of formula (I) as defined in claim 1 by process step variant (a) as defined in claim 1, which comprises the reaction of a compound of formula (II) wherein $R_2$ and $R_3$ are as defined in claim 1 with a compound of the formula (III) wherein one of $R_4$ and $R_5$ is hydrogen and the other is methyl or phenyl, both of $R_4$ and $R_5$ are methyl or $R_4$ and $R_5$ together are cyclohexyl, followed by transesterification of the resulting compound of formula (IV) by reaction with an alcohol of formula (VII):

$$R_1\text{-OH} \qquad (VII)$$

wherein: $R_1$ is $C_{1-4}$ alkyl, and, as necessary or desired, interconverting $R_1$, $R_2$ and $R_3$ in the resulting compound of formula (I) to further values of $R_1$, $R_2$ and $R_3$ as defined for formula (I) in claim 1.

3. A compound of formula (I) or a salt thereof:

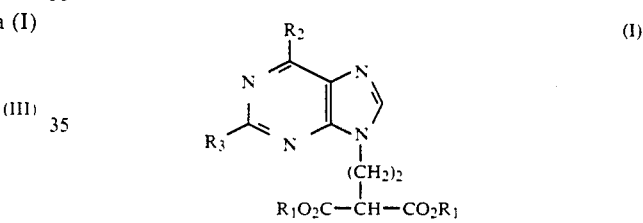

wherein $R_1$, $R_2$ and $R_3$ are as defined in claim 1.

4. A compound according to claim 3 or a salt thereof, wherein $R_1$ is methyl or ethyl; $R_2$ is hydrogen or methoxy; and $R_3$ is amino.

5. A compound of formula (IV) or a salt thereof:

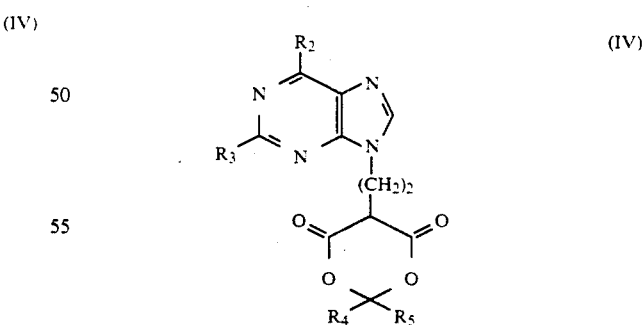

wherein: $R_2$, $R_3$, $R_4$ and $R_5$ are as defined in claim 1.

6. A compound according to claim 5 or a salt thereof, wherein $R_2$ is hydrogen or chlorine; $R_3$ is amino, acetylamino or chlorine; one of $R_4$ and $R_5$ is hydrogen and the other is phenyl, $R_4$ and $R_5$ are both methyl, or $R_4$ and $R_5$ together are cyclohexyl.

7. A compound of formula (VI) or a salt thereof:

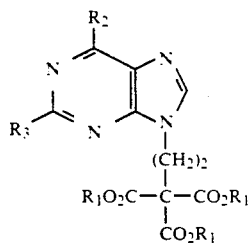

(VI)

wherein $R_1$ is $C_{1-6}$ alkyl or phenyl $C_{1-6}$ alkyl in which the phenyl group is optionally substituted; $R_2$ is hydrogen, hydroxy, chlorine, $C_{1-6}$ alkoxy, phenyl $C_{1-6}$ alkoxy, or amino; and $R_3$ is halogen, $C_{1-6}$ alkylthio, $C_{1-6}$ alkylsulphonyl, azido, an amino group, or a protected amino group.

8. A compound according to claim 7 or a salt thereof, wherein $R_1$ is ethyl; $R_2$ is hydrogen or chlorine and $R_3$ is amino.

* * * * *